(12) United States Patent
Iwasaki

(10) Patent No.: US 10,188,276 B2
(45) Date of Patent: Jan. 29, 2019

(54) CLEANING AUXILIARY TOOL

(71) Applicant: OLYMPUS CORPORATION, Tokyo (JP)

(72) Inventor: Tomokazu Iwasaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 27 days.

(21) Appl. No.: 15/293,794

(22) Filed: Oct. 14, 2016

(65) Prior Publication Data

US 2017/0027431 A1 Feb. 2, 2017

Related U.S. Application Data

(60) Division of application No. 14/878,308, which is a continuation of application No. PCT/JP2014/078222, filed on Oct. 23, 2014, now Pat. No. 9,492,066.

(30) Foreign Application Priority Data

Feb. 20, 2014 (JP) .................................. 2014-030897

(51) Int. Cl.
  *A61B 1/00* (2006.01)
  *A61B 1/12* (2006.01)
  (Continued)

(52) U.S. Cl.
  CPC .......... *A61B 1/122* (2013.01); *A61B 1/00068* (2013.01); *A61B 1/125* (2013.01);
  (Continued)

(58) Field of Classification Search
  CPC ....... A61B 1/12–1/125; A61B 1/00057; A61B 1/00137; A61B 1/00068; A61M 39/10; A61M 39/12
  See application file for complete search history.

(56) References Cited

U.S. PATENT DOCUMENTS

2006/0135851 A1 6/2006 Yamazaki
2011/0298169 A1 12/2011 Nguyen et al.

FOREIGN PATENT DOCUMENTS

EP 0 106 310 A2 4/1984
EP 1 762 172 A2 3/2007
(Continued)

OTHER PUBLICATIONS

Extended Supplementary European Search Report dated Oct. 28, 2016 in related European Patent Application No. 14 88 3457.5.
(Continued)

*Primary Examiner* — Spencer E Bell
(74) *Attorney, Agent, or Firm* — Scully, Scott, Murphy & Presser, P.C.

(57) ABSTRACT

A separator unit is a cleaning auxiliary tool to be inserted into an air/water feeding cylinder. The separator unit includes a partition plate for partitioning an air feeding conduit side and a water feeding conduit side, and two elastic members in an air/water feeding cylinder. The two elastic members are arranged at an outer circumferential side of the partition plate. When an internal pressure on the air feeding conduit side corresponds to an internal pressure on the water feeding conduit side, the elastic members are spaced apart from an inner wall of the air/water feeding cylinder by a predetermined distance, and when one of the internal pressures on the air feeding conduit and the water feeding conduit becomes higher than the other, one of the elastic members is deformed by receiving the higher internal pressure and comes in close contact with the inner wall of the air/water feeding cylinder.

3 Claims, 16 Drawing Sheets

(51) Int. Cl.
*A61B 90/70* (2016.01)
*B08B 9/027* (2006.01)
*B08B 9/053* (2006.01)

(52) U.S. Cl.
CPC .............. *A61B 90/70* (2016.02); *B08B 9/027* (2013.01); *B08B 9/053* (2013.01); *A61B 2090/701* (2016.02)

(56) References Cited

FOREIGN PATENT DOCUMENTS

| JP | 2000-070218 A | 3/2000 |
| JP | 2010-029467 A1 | 2/2010 |
| JP | 2012-505032 A | 3/2012 |
| WO | WO 2010/045051 A1 | 4/2010 |

OTHER PUBLICATIONS

International Search Report dated Jan. 20, 2015 issued in PCT/JP2014/078222.

CLEANING AUXILIARY TOOL

CROSS REFERENCE TO RELATED APPLICATION

This application is a divisional application of U.S. application Ser. No. 14/878,308 filed on Oct. 8, 2015, which is a continuation application of PCT/JP2014/078222 filed on Oct. 23, 2014 and claims benefit of Japanese Application No. 2014-030897 filed in Japan on Feb. 20, 2014, the entire contents of each of which are incorporated herein by reference.

BACKGROUND OF INVENTION

1. Field of the Invention

The present invention relates to a cleaning auxiliary tool for use in cleaning and disinfecting an endoscope.

2. Description of the Related Art

Conventionally, an endoscope is cleaned and disinfected by a cleaning and disinfecting apparatus after use. In an insertion portion of the endoscope, an air feeding conduit and a water feeding conduit are inserted through, and in the cleaning and disinfecting apparatus, cleaning and disinfecting of the air feeding conduit and the water feeding conduit are also performed.

In an operation portion of the endoscope, an air/water feeding cylinder is disposed, and the air/water feeding cylinder (hereinafter also referred to simply as "cylinder") is formed as a concave portion having an opening and a bottom portion. On an inner wall of the cylinder, two openings for the air feeding conduit and two openings for the water feeding conduit are formed, and the air feeding conduit and the water feeding conduit communicate with each other in the cylinder. A button for air feed and water feed (hereinafter referred to as "air feed/water feed button") is fitted in the cylinder, and a surgeon can perform the air feed and the water feed to the insertion portion of the endoscope by operating the air feed/water feed button.

When cleaning and disinfecting the endoscope, the air feed/water feed button is removed from the cylinder and a cleaning adapter is attached to the cylinder and thereafter the endoscope is cleaned and disinfected.

Further, if a foreign matter gets into the air feeding conduit or the water feeding conduit to clog the conduit, cleaning performance and disinfection performance in the air feeding conduit or the water feeding conduit cannot be secured. Therefore, a cleaning and disinfecting apparatus having a function of detecting clogging of the conduit using flow rate sensors respectively provided in the air feeding conduit and the water feeding conduit has been proposed.

In a case where liquids flowing in the air feeding conduit and the water feeding conduit meet in the cylinder, even if there is clogging in one of the air feeding conduit and the water feeding conduit, the flow rate sensors cannot detect the clogging, and therefore a separator for separating the air feeding conduit and the water feeding conduit from each other in the cylinder has been proposed, as disclosed in Japanese Translation of PCT Application Publication No. 2012-505032. The separator separates passages of the air feeding conduit and the water feeding conduit in the cylinder and thereby enables detection of the clogging of the respective conduits of the air feeding conduit and water feeding conduit.

SUMMARY OF THE INVENTION

A cleaning auxiliary tool according to an aspect of the present invention is to be inserted into a bottomed cylinder having a bottomed cylindrical shape, the bottomed cylinder having a first opening through which a fluid from a first conduit is introduced, the first conduit being inserted through an endoscope, a second opening through which the fluid is led out into the first conduit, a third opening through which the fluid from a second conduit is introduced, the second conduit running in parallel with the first conduit in the endoscope, and a fourth opening through which the fluid is led out into the second conduit, the cleaning auxiliary tool including: a lid portion that closes an opening of the bottomed cylinder; a shaft portion having a first end portion connected to the lid portion and a second end portion extending into the bottomed cylinder; a partition portion that is provided on a side of the second end portion of the shaft portion and positioned between the first opening and the third opening and between the second opening and the fourth opening, and partitions a side of the first conduit and a side of the second conduit with a gap forming a space of a predetermined distance from an inner wall of the bottomed cylinder; and a close contact portion that is arranged on an outer circumferential side of the partition portion, is spaced apart from the inner wall of the bottomed cylinder by the predetermined distance when an internal pressure on the side of the first conduit corresponds to an internal pressure on the side of the second conduit, is deformed by receiving the internal pressure on the side of the first conduit and comes in close contact with the inner wall of the bottomed cylinder when the internal pressure on the side of the first conduit becomes higher than the internal pressure on the side of the second conduit, and is deformed by receiving the internal pressure on the side of the second conduit and comes in close contact with the inner wall of the bottomed cylinder when the internal pressure on the side of the second conduit becomes higher than the internal pressure on the side of the first conduit.

A cleaning auxiliary tool according to another aspect of the present invention is to be inserted into a bottomed cylinder having a bottomed cylindrical shape with one end opened and other end closed, the bottomed cylinder having a first opening through which a fluid from a first conduit is introduced, the first conduit being inserted through an endoscope, a second opening through which the fluid is led out into the first conduit, a third opening through which the fluid from a second conduit is introduced, the second conduit running in parallel with the first conduit in the endoscope, and a fourth opening through which the fluid is led out into the second conduit, the cleaning auxiliary tool including: a lid portion that closes an opening of the bottomed cylinder; a shaft portion having a first end portion connected to the lid portion and a second end portion extending into the bottomed cylinder; and a partition portion that is provided on a side of the second end portion of the shaft portion and positioned between the first opening and the third opening and between the second opening and the fourth opening, partitions a side of the first conduit and a side of the second conduit in a state of being in close contact with an inner wall of the bottomed cylinder, moves toward the second end portion of the shaft portion by receiving an internal pressure on the side of the first conduit when the internal pressure on side of the first conduit becomes higher than an internal pressure on the side of the second conduit, and moves toward the first end portion of the shaft portion by receiving the internal pressure on the side of the second conduit when the internal pressure on the side of the second conduit becomes higher than the internal pressure on the side of the first conduit.

A cleaning auxiliary tool according to still another aspect of the present invention is to be inserted into a bottomed cylinder having a bottomed cylindrical shape, the bottomed cylinder having a first opening through which a fluid from a first conduit is introduced, the first conduit being inserted through an endoscope, a second opening through which the fluid is led out into the first conduit, a fourth opening through which the fluid introduced from the first conduit is led out into a second conduit which runs in parallel with the first conduit from an intermediate position of the first conduit in the endoscope, the cleaning auxiliary tool including: a lid portion that closes an opening of the bottomed cylinder; a shaft portion that penetrates the lid portion, has a tubular shape and has a first end portion opened outside of the bottomed cylinder and a second end portion opened in the bottomed cylinder; a partition portion that is provided at the shaft portion and positioned between the first opening and the fourth opening and between the second opening and the fourth opening, and partitions a side of first conduit and a side of the second conduit with a gap forming a space of a predetermined distance from an inner wall of the bottomed cylinder; and a close contact portion that is arranged on an outer circumferential side of the partition portion, is spaced apart from the inner wall of the bottomed cylinder by the predetermined distance when an internal pressure at the side of the first conduit corresponds to an internal pressure on the side of the second conduit, is deformed by receiving the internal pressure on the side of the first conduit and comes in close contact with the inner wall of the bottomed cylinder when the internal pressure on the side of the first conduit becomes higher than the internal pressure on the side of the second conduit, and is deformed by receiving the internal pressure on the side of the second conduit and comes in close contact with the inner wall of the bottomed cylinder when the internal pressure on the side of the second conduit becomes higher than the internal pressure on the side of the first conduit.

DETAILED DESCRIPTION OF THE PREFERRED EMBODIMENT(S)

Figure 1:
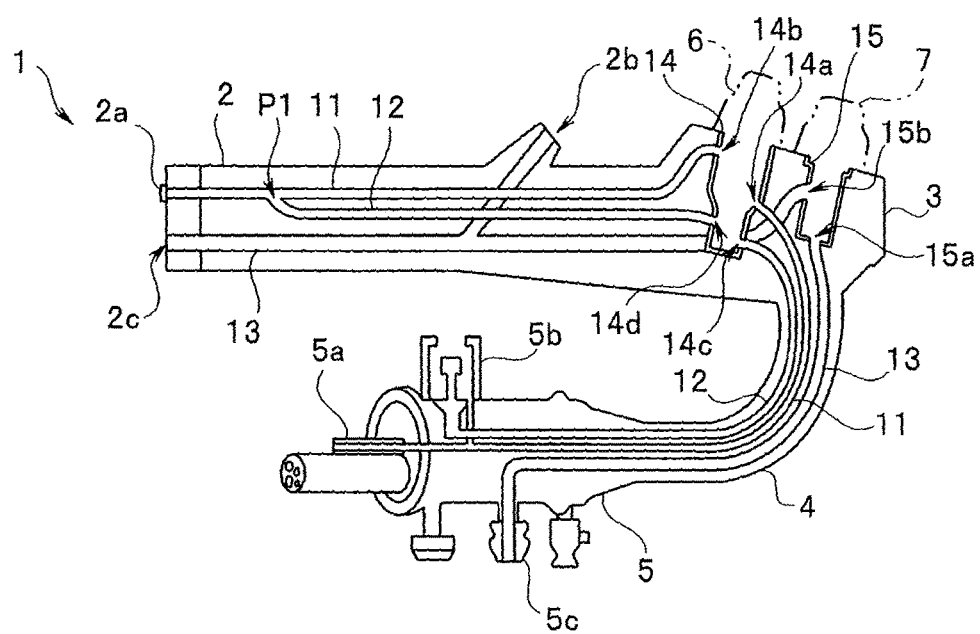
FIG. 1 is a schematic configuration diagram of an endoscope for explaining conduits in the endoscope according to a first embodiment of the present invention.

Hereinafter, embodiments of the present invention will be described referring to the drawings.

It is noted that, in the drawings for use in the following description, contraction scales are made different for respective elements in order to make each of the elements have a degree of size recognizable on the drawings, and the present invention is not limited only to configurations having the number of elements, shapes of the elements, ratios of sizes of the elements and relative positional relations between the elements that are shown in the drawings.

First Embodiment (Configuration of Endoscope)

FIG. 1 is a schematic configuration diagram of an endoscope for explaining conduits in the endoscope.

Since the endoscope 1 is one that is well known, a configuration of the endoscope 11 is not particularly limited and thus detailed description of the configuration is omitted. The endoscope 1 is configured to mainly include an insertion portion 2 to be inserted into a subject, an operation portion 3 provided on a proximal end side of the insertion portion 2, a universal cord 4 extending from the operation portion 3 and a connector portion 5 provided at the universal cord 4. The connector portion 5 is connected to external apparatuses such as a video processor, a water feeding tank or a suction apparatus.

In the insertion portion 2 of the endoscope 1, three conduits, i.e. an air feeding conduit 11, a water feeding conduit 12 and a suction channel 13 are inserted through. At a distal end side of the operation portion 3, a forceps insertion port 2b is provided and the forceps insertion port 2b communicates with the suction channel 13 which is also a forceps channel.

A distal end portion of the air feeding conduit 11, which is a first conduit, is connected to a nozzle 2a provided at a distal end portion of the insertion portion 2. A proximal end portion of the air feeding conduit 11 is connected to a connection portion 5a of the connector portion 5. A distal end portion of the water feeding conduit 12, which is a second conduit, is connected to the air feeding conduit 11 at an intermediate position P1 thereof, so that the water feeding conduit 12 and the air feeding conduit 11 are confluent to communicate with each other. The nozzle 2a is connected to a confluent conduit. A proximal end portion of the water feeding conduit 12 is connected to a connection portion 5b of the connector portion 5. A distal end portion of the suction channel 13 is connected to a suction port 2c which is provided at the distal end portion of the insertion portion 2 and also serves as a forceps port, and a proximal end portion of the suction channel 13 is connected to a connection portion 5c of the connector portion 5.

When using the endoscope 1, the endoscope 1 is connected to a light source apparatus which is provided with an air feeding device such as an air tank or an air feeding pump, and the connection portion 5b is connected to a liquid feeding device such as a liquid feeding tank. The connection portion 5c is connected to a suction apparatus such as a suction pump.

At the operation portion 3, an air/water feeding cylinder 14 to which an air/water feeding button 6 (indicated by the two-dot chain line) is attached, and a suction cylinder 15 to which a suction button 7 (indicated by the two-dot chain line) are provided. Each of the air/water feeding cylinder 14 and the suction cylinder 15 has a bottomed cylindrical shape with one end opened on a surface of an external member of the operation portion 3, and the other end closed.

The cylinder 14 is provided in the middle of the air feeding conduit 11 and in the middle of the water feeding conduit 12. The suction cylinder 15 is provided in the middle of the suction channel 13 which is a suction conduit.

Specifically, the cylinder 14 is arranged in the middle of the air feeding conduit 11 and in the middle of the water feeding conduit 12, and is connected to the air feeding conduit 11 and the water feeding conduit 12 such that an inner space of the cylinder 14 communicates with the respective insides of the air feeding conduit 11 and the water feeding conduit 12. Thus, in the cylinder 14, a first opening 14a and a second opening 14b which communicate with the air feeding conduit 11, and a third opening 14c and a fourth opening 14d which communicate with the water feeding conduit 12 are formed.

The suction cylinder 15 is arranged in the middle of the suction channel 13 which is the suction conduit, and is connected to the suction channel 13 such that an inner space of the suction cylinder 15 communicates with the inside of the suction channel 13. Thus, in the suction cylinder 15, two openings 15a and 15b which communicate with the suction channel 13 are formed.

A surgeon can perform air feeding and water feeding from the nozzle 2a provided at the distal end portion of the insertion portion 2 by operating the air/water feeding button 6 attached to the cylinder 4, and can perform suction from the suction port 2c provided at the distal end portion of the insertion portion 2 by operating the suction button 7 attached to the suction cylinder 15.

When the endoscope 1 is to be cleaned and disinfected after the endoscope 1 is used, cleaning auxiliary tools are respectively attached to the cylinders 14 and 15 from which the air/water feeding button 6 and the suction button 7 are detached, and the endoscope 1 is cleaned and disinfected by a cleaning and disinfecting apparatus. There is a cleaning and disinfecting apparatus of a type in which a flow rate sensor is provided at an outlet side of a disinfection solution and clogging of the conduit is detected on the basis of change in a flow rate. However, in a case where the air feeding conduit 11 and the water feeding conduit 12 communicate with each other in the cylinder, if one of the conduits is clogged, the disinfection solution escapes through the other of the conduits so that the flow rate does not change, and therefore it is hard to detect conduit clogging. Therefore, a separator unit having a mechanism for partitioning a passage of the air feeding conduit 11 and a passage of the water feeding conduit 12 is used as a cleaning auxiliary tool.

(Configuration of Separator Unit)

Figure 2:
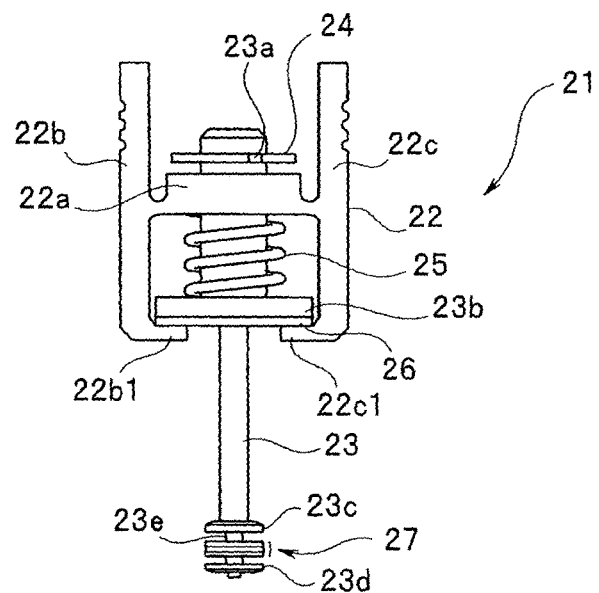
FIG. 2 is a front view of a separator unit 21 according to the first embodiment of the present invention.
Figure 3:
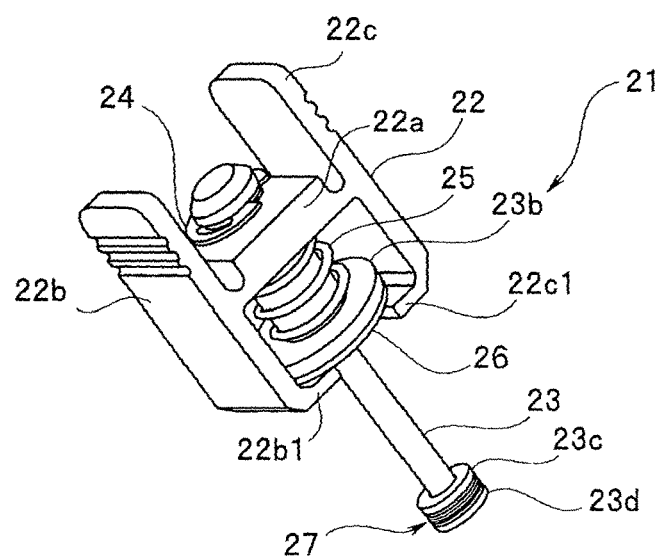
FIG. 3 is a perspective view of the separator unit 21 according to the first embodiment of the present invention.
Figure 4:
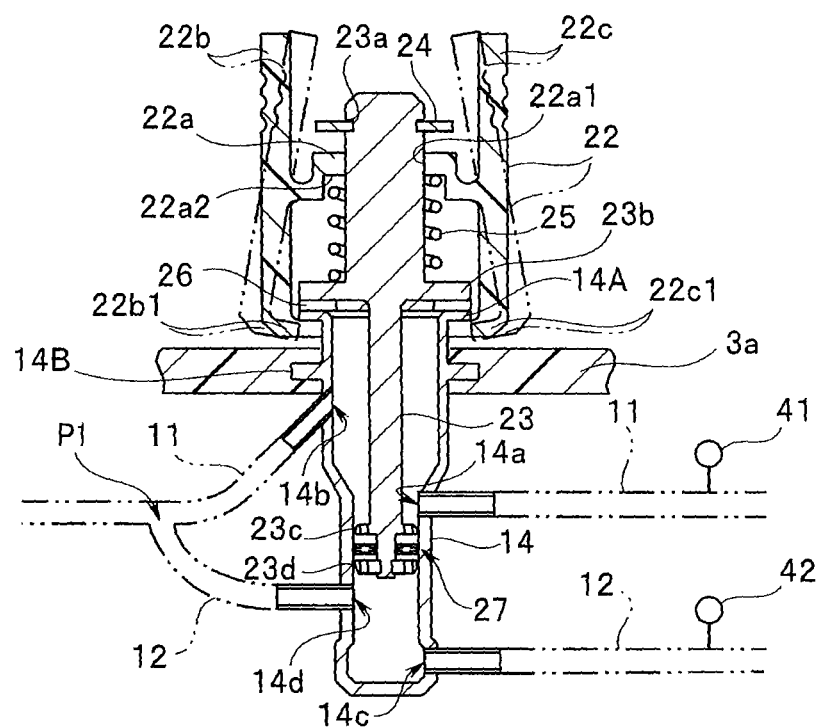
FIG. 4 is a cross sectional view of the separator unit 21, which is attached to a cylinder 14 in an operation portion 3, along an axial direction of a shaft portion according to the first embodiment of the present invention.

FIG. 2 is a front view of a separator unit 21 according to the present embodiment. FIG. 3 is a perspective view of the separator unit 21 according to the present embodiment. FIG. 4 is a cross sectional view of the separator unit 21, which is attached to the cylinder 14 in the operation portion 3, along an axial direction of a shaft portion.

The separator unit 21 is a cleaning auxiliary tool configured to include a fixing member 22 and a shaft portion 23.

The fixing member 22 has a H-shaped cross section as shown in FIG. 2. The fixing member 22 has elasticity and is made of resin, for example, although a material thereof is not limited. More specifically, polyacetal which is excellent in chemical resistance is cited. The fixing member 22 has arm portions 22b and 22c on both sides of a central portion 22a. The arm portions 22b and 22c have extending portions 22b1 and 22c1, respectively, at distal end portions thereof, the extending portions 22b1 and 22c1 extending to be close to each other. Since the fixing member 22 has elasticity, when proximal end portions of the arm portions 22b and 22c are brought close to each other, the extending portions 22b1 and 22c1 at the distal end portions of the arm portions 22b and 22c are spaced apart from each other, as shown by the two-dot chain line in FIG. 4.

As shown in FIG. 4, the fixing member 22 has a hole 22a1 at the central portion 22a, which is formed to be parallel to axial directions of the arm portions 22b and 22c. The shaft portion 23 is inserted through the hole 22a1. At a proximal end portion of the shaft portion 23, a circumferential groove 23a is formed. An E-ring 24 for retaining the shaft portion 23 is fixed by being fitted into the groove 23a on a proximal end side of the central portion 22a.

At a distal end side of the central portion 22a, a concave portion 22a2 is formed. The shaft portion 23 has an outward flange 23b at a central portion. A coil spring 25 is provided in such a manner as to wind on an outer circumferential portion of the shaft portion 23. The coil spring 25 is provided in a compressed state between the outward flange 23b and the concave portion 22a2 such that one end of the coil spring 25 enters the concave portion 22a2 and the other end of the coil spring 25 presses a proximal-end-side surface of the outward flange 23b.

An annular seal member 26 is provided as being adhered to a distal-end-side surface of the outward flange 23b. Although a material of the shaft portion 23 is not particularly limited, the shaft portion 23 is a cylindrical member made of metal such as stainless steel which is excellent in chemical resistance, and is inserted through a hole at a center of the annular seal member 26.

Figure 5:
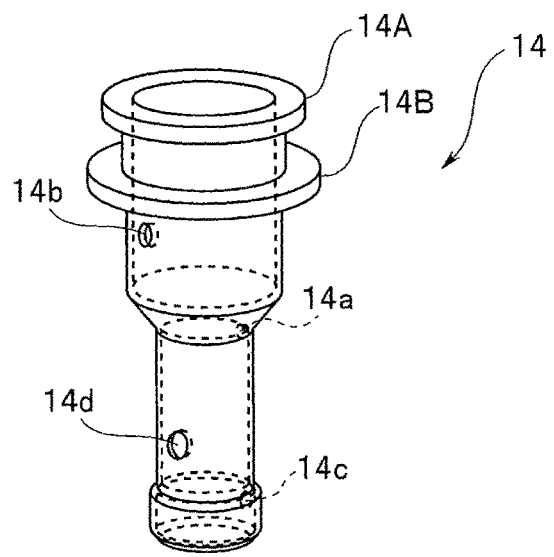
FIG. 5 is a perspective view of the cylinder 14 according to the first embodiment of the present invention.

Here, the configuration of the cylinder 14 to which the separator unit 21 is attached will be described. FIG. 5 is a perspective view of the cylinder 14, and FIG. 6 is a cross sectional view showing a state of the cylinder 14 fixed in the operation portion 3.

Figure 6:
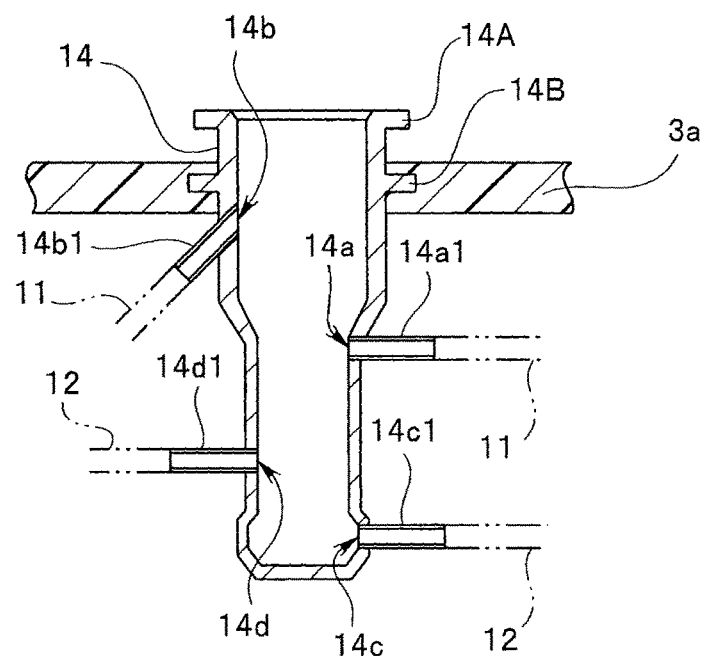
FIG. 6 is a cross sectional view of the cylinder 14 fixed in the operation portion 3 according to the first embodiment of the present invention.

The cylinder 14 is fixed to an external member 3a of the operation portion 3 as shown in FIGS. 4 and 6. The cylinder 14 has a shape of a bottomed cylinder with one end opened and the other end closed.

The cylinder 14 has a mouthpiece 14A to which the separator unit 21 is attached and fixed, at a proximal end portion of the cylinder 14. On a distal end side of the mouthpiece 14A, an outward flange 14B is formed, and the cylinder 14 is fixed to the operation portion 3 such that outward flange 14B is embedded in the external member 3a of the operation portion 3.

As shown in FIG. 5, the first opening 14a and the second opening 14b are formed on a side wall of the cylinder 14 at an opening side thereof. The third opening 14c and the fourth opening 14d are formed on the side wall of the cylinder 14 at an bottom side thereof. As shown in FIG. 6, the first opening 14a, the second opening 14b, the third opening 14c and the fourth opening 14d are provided with connection portions 14a1, 14b1, 14c1 and 14d1, respectively, the air feeding conduit 11 is connected to the connection portions 14a1 and 14b1, and the water feeding conduit 12 is connected to the connection portions 14c1 and 14d1.

The first opening 14a is an air-feeding-conduit-side fluid inlet port as an opening on an upstream side which is connected to the air feeding device and through which a gas is introduced. The second opening 14b is an air-feeding-conduit-side fluid outlet port as an opening on a downstream side from which the gas is led out. The third opening 14c is a water-feeding-conduit-side fluid inlet port as an opening on the upstream side which is connected to a water feeding device and through which a liquid is introduced. The fourth opening 14d is a water-feeding-conduit-side fluid outlet port as an opening on the downstream side from which the liquid is led out. Thus, the cylinder 14 is the bottomed cylinder having the first opening 14a from which the fluid from the air feeding conduit 11 inserted through the endoscope 1 is introduced, the second opening 14b through which the fluid is led out into the air feeding conduit 11, the third opening 14c through which the fluid from the water feeding conduit 12 is introduced, the water feeding conduit 12 running in parallel with the air feeding conduit 11 in the endoscope, and the fourth opening 14d through which the fluid is led out into the water feeding conduit 12.

As mentioned above, in the state where the proximal end portions of the arm portions 22b and 22c are brought close to each other, so that the extending portions 22b1 and 22c1 are separated from each other (as shown by the two-dot chain line in FIG. 4), when the proximal end portions of the arm portions 22b and 22c, which are brought close to each other, are made be separate from each other while pressing the outward flange 23b of the shaft portion 23 toward the mouthpiece 14A, the extending portions 22b1 and 22c1 enter the lower side of the mouthpiece 14A. As a result, the separator unit 21 is attached to the mouthpiece 14A in a state where the coil spring 25 presses the outward flange 23b toward the distal end side and the seal member 26 seals a space between the outward flange 23b and the mouthpiece 14A.

Thus, the outward flange 23b constitutes a lid portion that closes the opening of the cylinder 14 which is the bottomed cylinder. Further, the shaft portion 23 has one end connected to the outward flange 23b and the other end extending into the cylinder 14.

Figure 7:
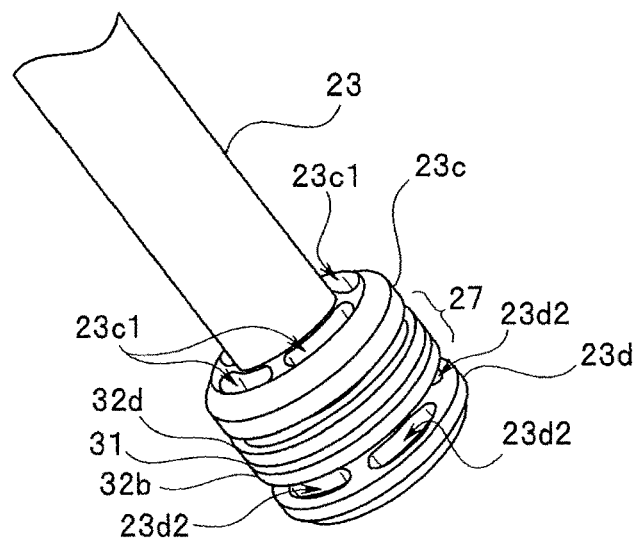
FIG. 7 is a perspective view of a distal end portion of a shaft portion 23 according to the first embodiment of the present invention.
Figure 8:
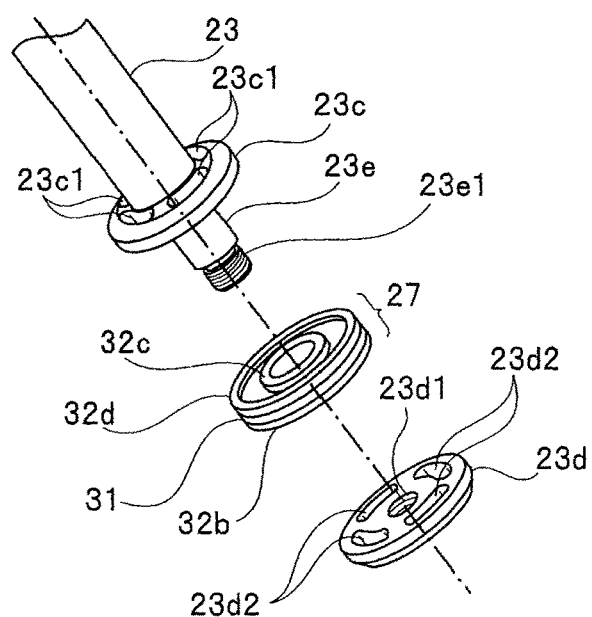
FIG. 8 is an exploded view of the distal end portion of the shaft portion 23 according to the first embodiment of the present invention.

Next, configuration of a distal end portion of the shaft portion 23 of the separator unit 21 will be described. FIG. 7 is a perspective view of the distal end portion of the shaft portion 23, and FIG. 8 is an exploded view of the distal end portion of the shaft portion 23.

At the distal end portion of the shaft portion 23, two outward flanges 23c and 23d are provided. The outward flange 23d is formed as a separate member with respect to the shaft portion 23. A partition plate 27 in an annular shape is a movable member which is provided between the outward flanges 23c and 23d in a manner such that the shaft portion 23 is inserted through a hole at a central portion of the partition plate 27 in a loosely fitted state.

The outward flange 23c is formed to be somewhat proximal with respect to a distal end of the shaft portion 23, and the shaft portion 23 has an extending part 23e which extends to be distal with respect to the outward flange 23c. At a distal end portion of the extending part 23e, a male screw portion 23e1 is formed. A female screw portion 23d1, which is formed on an inner circumferential surface of an annular member constituting the outward flange 23d, is screw-engaged with the male screw portion 23e1 of the extending part 23e, and thereby the outward flange 23d is formed at the distal end portion of the shaft portion 23. Besides, it may be configured that the outward flange 23c is also formed as a separate member with respect to the shaft portion 23 and is fixed to the shaft portion 23.

A partition portion is constituted by the outward flange 23d as a plate member fixed to the shaft member 23, the outward flange 23c as a plate member which is provided at the shaft portion 23 and arranged to be closer to the air feeding conduit 11 than the outward flange 23d, and the partition plate 27 which has an annular shape with an inner diameter larger than an outer diameter of the shaft portion 23, is arranged between the outward flanges 23c and 23d in the state where the shaft portion 23 is inserted through the hole at the central portion of the annular shape, and moves along the shaft portion 23 toward one of the air feeding conduit 11 and the water feeding conduit 12, whichever has a lower inner pressure.

As shown in FIG. 4, an inner diameter of a distal end side part of the cylinder 14 is smaller than an inner diameter a proximal end side part of the cylinder 14. The separator unit 21 is attached to the cylinder 14 by being inserted from the opening side of the cylinder 14. The outward flanges 23c and 23d are formed and provided at the shaft portion 23 such that the outward flanges 23c and 23d are positioned between the first opening 14a and the third opening 14c and between second opening 14b and the fourth opening 14d in the cylinder 14 when the separator unit 21 is attached to the cylinder 14.

Outer diameters of the annular outward flanges 23c, 23d and the partition plate 27 are smaller than the inner diameter of the distal end side part of the cylinder 14. That is, a narrow gap g exists between outer circumferential surfaces of the outward flanges 23c, 23d and the partition plate 27, and an inner wall of the distal end side part of the cylinder 14.

A plurality of holes 23c1 are formed in the outward flange 23c. In the same manner, a plurality of holes 23d2 are formed also in the outward flange 23d.

The annular partition plate 27 is provided between the outward flanges 23c and 23d of the shaft portion 23 such that extending part 23e is inserted through the hole at the center of the partition plate 27 in the loosely fitted state.

Figure 9:
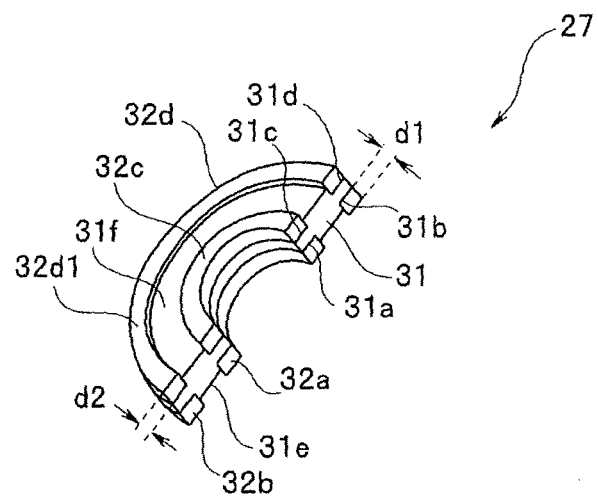
FIG. 9 is a cross-sectional perspective view of a partition plate 27 along an axial direction of the shaft portion 23 according to the first embodiment of the present invention.
Figure 10:
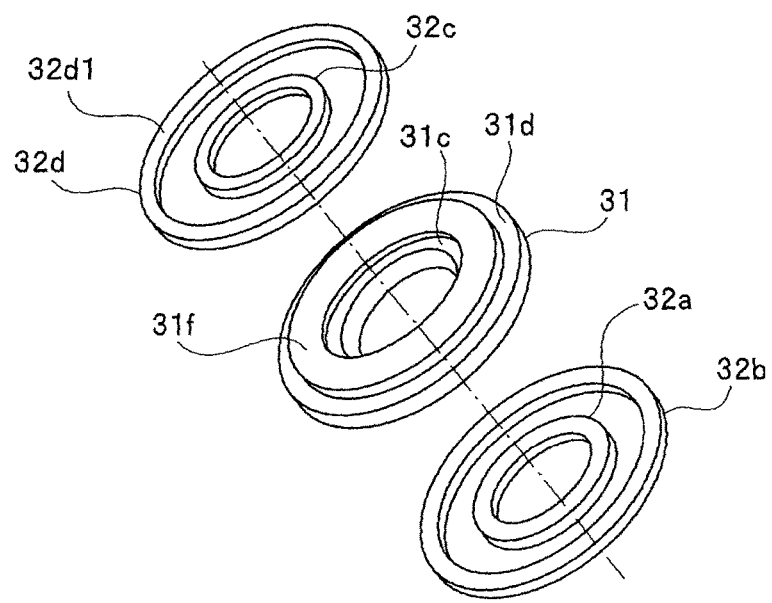
FIG. 10 is an exploded view of the partition plate 27 according to the first embodiment of the present invention.

FIG. 9 is a cross-sectional perspective view of the partition plate 27 along the axial direction of the shaft portion 23. FIG. 10 is an exploded view of the partition plate 27.

The partition plate 27 is constituted by an annular member 31 and four annular elastic members 32a, 32b, 32c and 32d (which are, hereinafter, referred to as elastic members 32 or elastic member 32 when referring to these four members as a whole or arbitrary one of the elastic members, respectively). The annular member 31 is made of resin or of metal such as stainless steel, and the elastic members 32 are made of rubber or silicone. As described later, the elastic members 32b and 32d are close contact portions which come in close contact with the inner wall of the cylinder 14, and constitute deformation portions made of a deformable material.

Notch portions 31a and 31b are formed on a distal-end-side surface of the annular member 31 at an inner peripheral portion and an outer peripheral portion, respectively. Notch portions 31c and 31d are formed on a proximal-end-side surface of the annular member 31 at an inner peripheral portion and an outer peripheral portion, respectively.

The elastic members 32a, 32b, 32c and 32d are adhered and fixed to the notch portions 31a, 31b, 31c and 31d by an adhesive. Outer diameters of the elastic members 32b and 32d are the same as a diameter of the annular member 31.

Further, the elastic member 32b has a thickness d1 such that a distal-end-side surface of the elastic member 32b, which is fixed to the notch portion 31b, protrudes from a distal-end-side surface 31e of the annular member 31 toward the distal end side. Similarly, the elastic member 32d has a thickness d2 such that a proximal-end-side surface of the elastic member 32d, which is fixed to the notch portion 31d, protrudes from a proximal-end-side surface 31f of the annular member 31 toward the proximal end side.

As mentioned above, the gap g, that has a cross sectional area S3 smaller than a cross sectional area S1 of the air feeding conduit 11 and a cross sectional area S2 of the water feeding conduit 12, exists between the outer circumferential surfaces of the outward flanges 23c, 23d and the partition plate 27, and the inner wall of the distal end side part of the cylinder 14 (see FIG. 11), and a space on a proximal end side of the outward flange 23c and a space on a distal end side of the outward flange 23d communicate with each other.

However, as described later, when the partition plate 27 moves in the axial direction of the shaft portion 23 by a pressure difference between the proximal end side and the distal end side of the partition plate 27 and the elastic member 32 is deformed by being pressed by the outward flange 23d or 23c, the diameter of the elastic member 32b or 32d is increased by a pressing force of the flange. When the diameter of the elastic member 32b or 32d is increased, the space on the proximal end side of the outward flange 23c and the space on the distal end side of the outward flange 23d become a state of not communicating with each other and being partitioned. That is, the elastic member 32b or 32d is deformed to increase the diameter thereof, and comes in close contact with the inner wall of the distal end side part of the cylinder 14, so that the gap is occluded. Thus, the elastic member 32b and 32 d each have the thickness, the outer diameter and softness such that the elastic member 32b or 32d comes in close contact with the inner wall of the distal end side part of the cylinder 14 when the elastic member 32b or 32d is pressed by the outward flange 23d or 23c.

As described above, the elastic member 32b is a deformation portion that is provided along the outer circumference of the partition plate 27 on the water feeding conduit 12 side, is crushed by being pressed by the outward flange 23d and the partition plate 27 to increase the outer diameter thereof, and comes in close contact with the inner wall of the cylinder 14. The elastic member 32d is a deformation portion that is provided along the outer circumference of the partition plate 27 on the air feeding conduit 11 side, is crushed by being pressed by the outward flange 23c and the partition plate 27 to increase the outer diameter thereof, and comes in close contact with the inner wall of the cylinder 14.

When the endoscope 1 is cleaned and disinfected, the liquid such as the cleaning solution flows in the air feeding conduit 11 and in the water feeding conduit 12. As shown in FIG. 4, a flow rate sensor 41 is connected to the air feeding conduit 11 at an upstream side thereof for measuring a flow rate of the liquid flowing through the air feeding conduit 11. A flow rate sensor 42 is connected to the water feeding conduit 12 at an upstream side thereof for measuring a flow rate of the liquid flowing in the water feeding conduit 12.

The upstream side herein referred to includes an endoscope cleaning and disinfecting apparatus which is connected to the endoscope, and the flow rate sensor 41 and the flow rate sensor 42 may be arranged in the endoscope cleaning and disinfecting apparatus, and if a cleaning tube is intervened between the endoscope and the endoscope cleaning and disinfecting apparatus, the sensors 41 and 42 may be arranged at the cleaning tube.

(Operation)

(In a Case where there is No Clogging in Both of the Air Feeding Conduit 11 and the Water Feeding Conduit)

When cleaning and disinfecting the endoscope 1, the liquid such as the cleaning solution is flowed simultaneously in the air feeding conduit 11 and the water feeding conduit 12. Since the cross sectional area S3 of the gap g between the inner wall of the cylinder 14 and the outer circumferential surface of the partition plate 27 in a cross section orthogonal to an axis of the shaft portion 23 is smaller than the cross sectional areas S1 and S2 of the air feeding conduit 11 and the water feeding conduit 12, respectively, the liquid that has entered from the first opening 14a flows into the second opening 14b, and the liquid that has entered from the third opening 14c flows into the fourth opening 14d. At this time, there is no pressure difference between the proximal end side and the distal end side of the partition plate 27, and the partition plate 27 does not move in the axial direction of the shaft portion 23.

Figure 11:
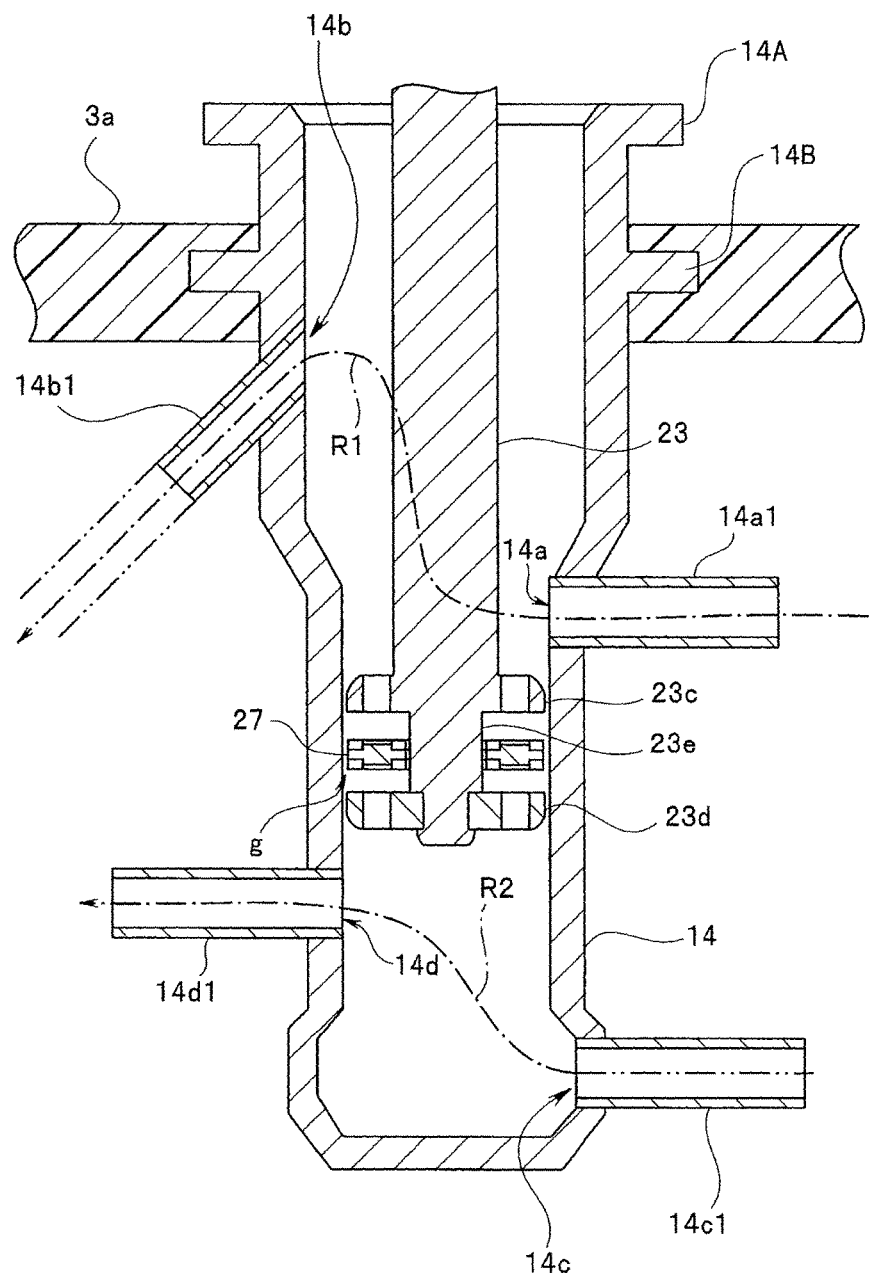
FIG. 11 is a cross sectional view of the distal end portion of the shaft portion 23 along the axial direction of the shaft portion 23 for explaining a state in which there is no clogging in the conduits when a liquid is simultaneously flowed in an air feeding conduit 11 and a water feeding conduit 12, according to the first embodiment of the present invention.

FIG. 11 is a cross sectional view of the distal end portion of the shaft portion 23 along the axial direction of the shaft portion 23 for explaining a state in which there is no clogging in the conduits when the liquid is flowed simultaneously in the air feeding conduit 11 and the water feeding conduit 12. The partition plate 27 is not pressed against either of the outward flanges 23c and 23d, and the liquid flowing through the air feeding conduit 11 flows from the first opening 14a to the second opening 14b along R1 shown by the chain line. In the same manner, the liquid flowing through the water feeding conduit 12 flows from the third opening 14a to the fourth opening 14d along R2 shown by the chain line. Thus, the liquid comes in contact with entirety of the inner wall of the cylinder 14 and the inside of the cylinder 14 is completely cleaned and disinfected.

As described above, the outward flanges 23c, 23d and the partition plate 27 constitute a partition portion that is provided at the distal end side of the shaft portion 23, positioned between the first opening 14a and the third opening 14c and between the second opening 14b and the fourth opening 14d, and partitions the air feeding conduit 11 side and the water feeding conduit 12 side with the gap g forming a space of a predetermined distance from the inner wall of the cylinder 14.

(In a Case where there is Clogging in the Air Feeding Conduit 11)

If there is clogging 90 in the air feeding conduit 11 between the second opening 14b of the cylinder 14 and the position P1, the liquid flowing through the air feeding conduit 11 does not flow into the second opening 14b. As a result, the pressure of the liquid in the cylinder 14 on the proximal end side of the partition plate 27 increases and the partition plate 27 is pressed toward the outward flange 23d by the liquid pressure. When the partition plate 27 is pressed against the outward flange 23d, the elastic member 32b is compressed in the axial direction of the shaft portion 23 by being pressed, and as a result the elastic member 32b is deformed to increase the diameter thereof, and closes the gap g between the outer circumferential surface of the elastic member 32b and the inner wall of the cylinder 14.

Figure 12:
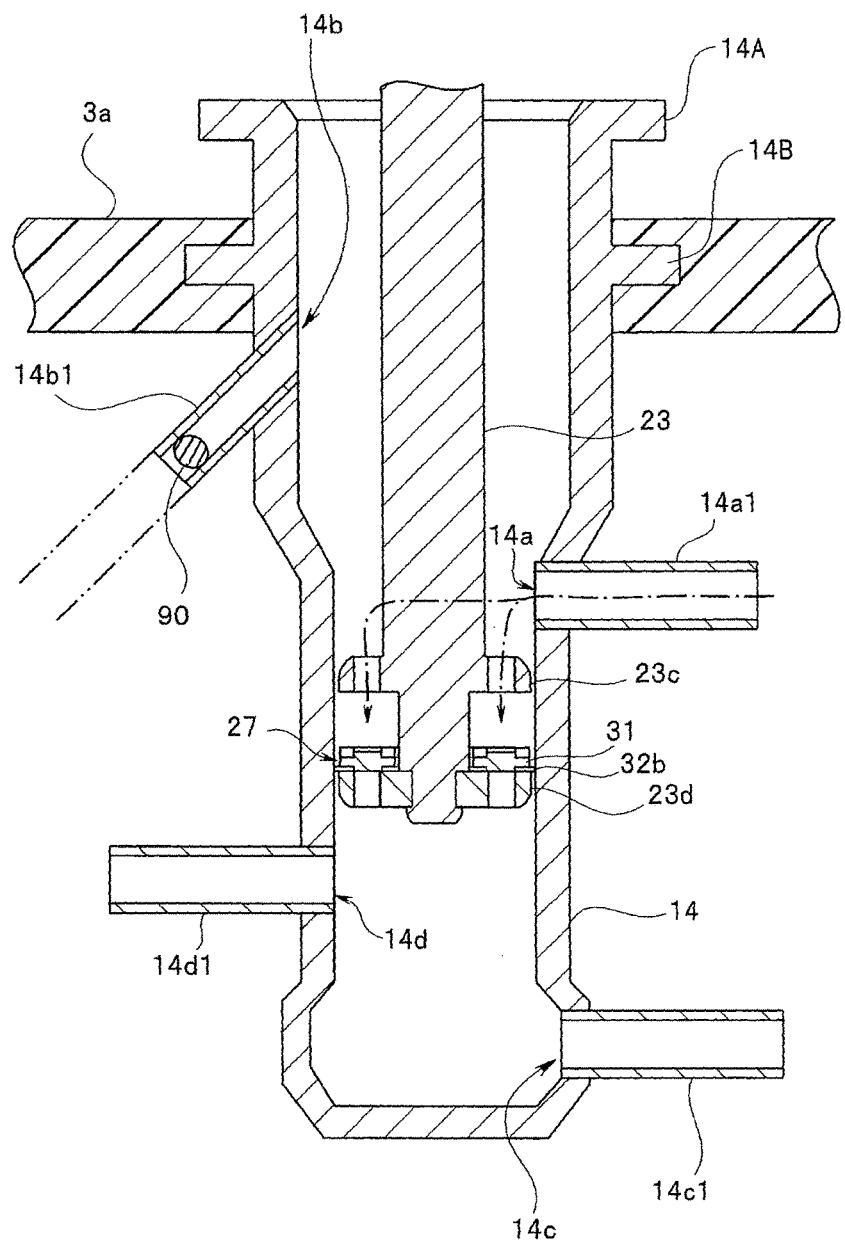
FIG. 12 is a cross sectional view of the distal end portion of the shaft portion 23 along the axial direction of the shaft portion 23 for explaining a state in which there is clogging in the air feeding conduit 11 between an opening 14b of the cylinder 14 and a position P1, according to the first embodiment of the present invention.

FIG. 12 is a cross sectional view of the distal end portion of the shaft portion 23 along the axial direction of the shaft portion 23 for explaining the state in which there is clogging in the air feeding conduit 11 between the second opening 14b of the cylinder 14 and the position P1. As shown by the chain line in FIG. 12, the partition plate 27 is pressed toward the outward flange 23d by the liquid, and the gap between the outer circumferential surface of the partition plate 27 and the inner wall of the distal end part of the cylinder 14 is closed by the elastic member 32b which is deformed to increase the diameter thereof. As a result, the flow of the liquid flowing through the air feeding conduit 11 is stopped, and therefore the flow rate measured by the flow rate sensor 41 becomes 0 (zero).

Thus, it is possible to detect that there is the clogging 90 in the air feeding conduit 11 between the second opening 14b of the cylinder 14 and the position P1.

It is noted that if there is clogging in the air feeding conduit 11 between the first opening 14a of the cylinder 14 and the flow rate sensor 41, the flow rate measured by the flow rate sensor 41 also becomes 0 (zero), and therefore it is possible to detect that there is clogging in the air feeding conduit 11.

(In a Case where there is Clogging in the Water Feeding Conduit 12)

If there is clogging 90 in the water feeding conduit 12 between the fourth opening 14d of the cylinder 14 and the position P1, the liquid flowing through the water feeding conduit 12 does not flow into the fourth opening 14d. As a result, the pressure of the liquid in the cylinder 14 on the distal end side of the partition plate 27 increases and the partition plate 27 is pressed toward the outward flange 23c. When the partition plate 27 is pressed against the outward flange 23c, the elastic member 32d is compressed in the axial direction of the shaft portion 23 by being pressed, and as a result the elastic member 32d is deformed to increase the diameter thereof, and closes the gap g between the outer circumferential surface of the elastic member 32d and the inner wall of the cylinder 14.

Figure 13:
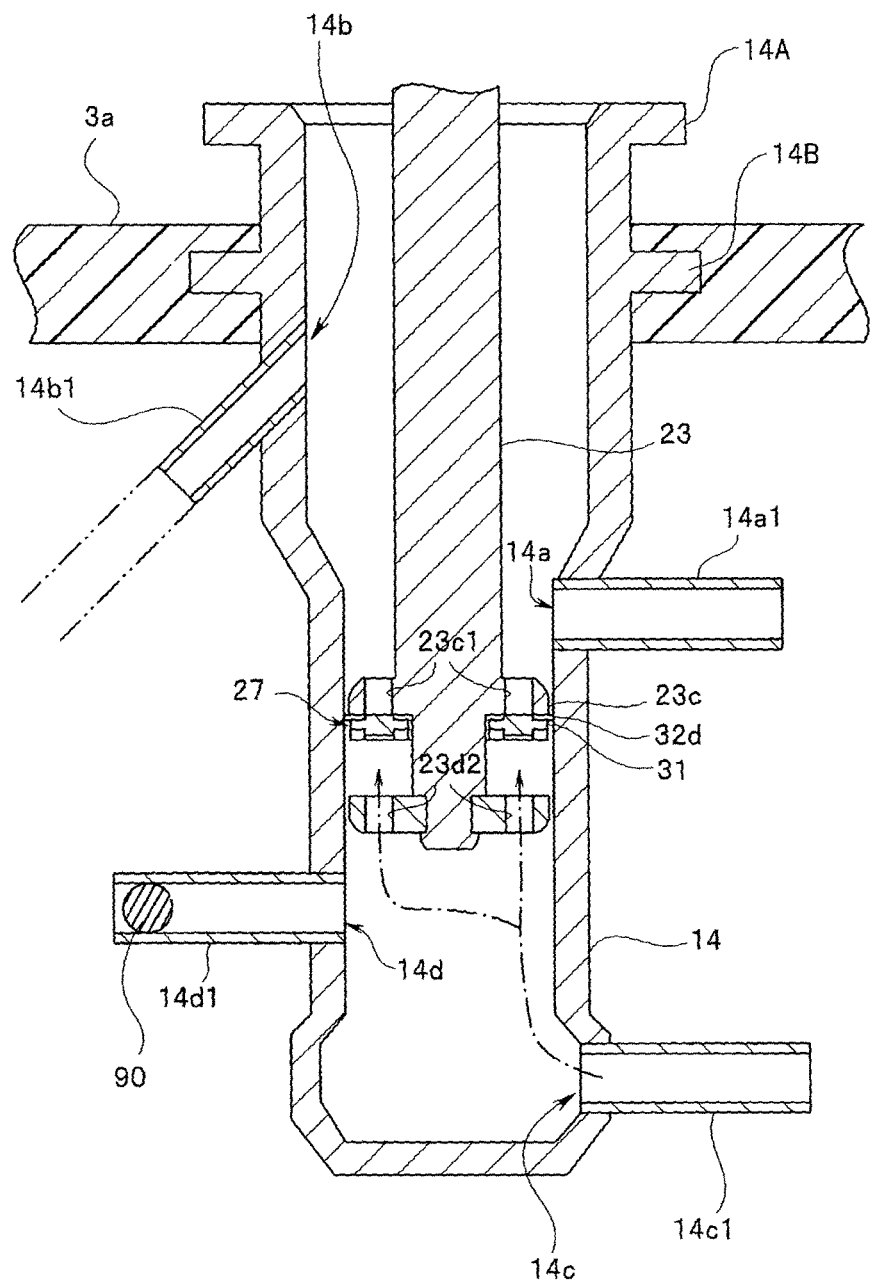
FIG. 13 is a cross sectional view of the distal end portion of the shaft portion 23 along the axial direction of the shaft portion 23 for explaining a state in which there is plugging in the water feeding conduit 12 between an opening 14d of the cylinder 14 and the position P1, according to the first embodiment of the present invention.

FIG. 13 is a cross sectional view of the distal end portion of the shaft portion 23 along the axial direction of the shaft portion 23 for explaining the state in which there is clogging in the water feeding conduit 12 between the fourth opening 14d of the cylinder 14 and the position P1. As shown by the chain line in FIG. 13, the partition plate 27 is pressed toward the outward flange 23c by the liquid, and the gap between the outer circumferential surface of the partition plate 27 and the inner wall of the distal end part of the cylinder 14 is closed by the elastic member 32d which is deformed to increase the diameter thereof. As a result, the flow of the liquid flowing through the water feeding conduit 12 is stopped, and therefore the flow rate measured by the flow rate sensor 41 becomes 0 (zero). Thus, it is possible to detect that there is the clogging 90 in the water feeding conduit 12 between the fourth opening 14d of the cylinder 14 and the position P1.

It is noted that if there is clogging in the water feeding conduit 12 between the third opening 14c of the cylinder 14 and the flow rate sensor 42, the flow rate measured by the flow rate sensor 42 also becomes 0 (zero), and therefore it is possible to detect that there is clogging in the water feeding conduit 12.

(In a Case where there is Clogging in the Conduit Downstream of the Position P1 where the Air Feeding Conduit 11 and the Water Feeding Conduit 12 Meet)

If there is clogging in the conduit downstream of the position P1 shown in FIG. 4, that is, in the confluent conduit, the liquid flowing through the air feeding conduit 11 and the water feeding conduit 12 does not flow into the second opening 14b and the fourth opening 14d. Therefore, in this case, both of the flow rates detected by the flow rate sensors 41 and 42 become 0 (zero), and it is possible to detect that there is clogging on a downstream side of the position P1 where the air feeding conduit 11 and the water feeding conduit 12 meet.

As described above, the elastic members 32b and 32d each constitute a close contact portion that is arranged at the outer circumferential side of the partition plate 27, is spaced apart from the inner wall of the cylinder 14 by the predetermined distance when the internal pressures on the air feeding conduit 11 side and the water feeding conduit 12 side in the cylinder 14 correspond to each other, is deformed by receiving the internal pressure on the air feeding conduit 11 side and comes in close contact with the inner wall of the cylinder 14 when the internal pressure on the air feeding conduit 11 side becomes higher than the internal pressure on the water feeding conduit 12 side, and is deformed by receiving the internal pressure on the water feeding conduit 12 side and comes in close contact with the inner wall of the cylinder 14 when the internal pressure on the water feeding conduit 12 side becomes higher than the internal pressure on the air feeding conduit 11 side.

Hence, according to the present embodiment, it is possible to provide the cleaning auxiliary tool that is capable of detecting clogging in each of the air feeding conduit and the water feeding conduit when performing the cleaning and disinfecting, and capable of cleaning and disinfecting the inner wall of the cylinder.

Modified Example 1

Figure 14:
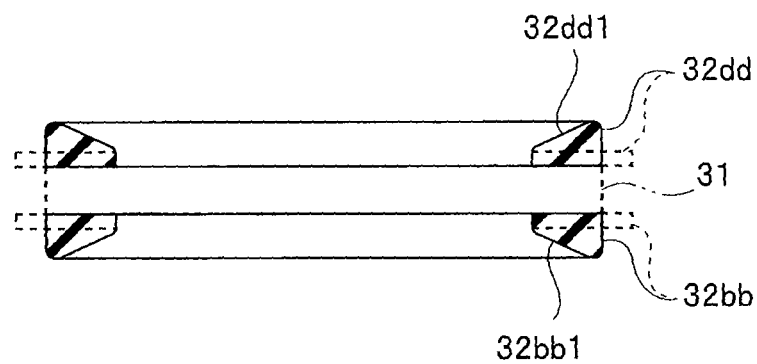
FIG. 14 is a cross sectional view of elastic members 32bb and 32dd along an axial direction of the cylinder 14 according to modified example 1 of the first embodiment of the present invention.

In the foregoing embodiment, cross sectional shapes of the elastic members 32b and 32d along the axial direction of the cylinder 14 are rectangular, but the cross sectional shapes of the elastic members 32b and 32d along the axial direction of the cylinder 14 need not be rectangular but each of the elastic members 32b and 32d may have a shape having an inclined surface with thickness decreasing toward the inside as shown in a modified example 1. FIG. 14 is a cross sectional view of elastic members 32bb and 32dd along the axial direction of the cylinder 14 according to the modified example 1. It is noted that the elastic members 32a and 32c are omitted and the annular member 31 is shown by the two-dot chain line in FIG. 14. In FIG. 14, the dotted line indicates the elastic members 32bb and 32dd when deformed.

As shown in FIG. 14, the elastic member 32bb, which is adhered to the notch portion 31b formed at the outer peripheral portion of the distal-end-side surface of the annular member 31, has an inclined surface 32bb1 with thickness of the annular elastic member 32bb decreasing toward a center thereof. Similarly, the elastic member 32dd, which is adhered to the notch portion 31d formed at the outer peripheral portion of the proximal-end-side surface of the annular member 31, has an inclined surface 32dd1 with thickness of the annular elastic member 32dd decreasing toward a center thereof.

Since the inclined surface 32bb1 as described above is provided on the elastic member 32bb, a diameter of the elastic member 32bb is easily increased radially when the elastic member 32bb is deformed by being pressed by the outward flange 23d. Also, since the inclined surface 32dd1 is provided on the elastic member 32dd, a diameter of the elastic member 32dd is easily increased radially when the elastic member 32dd is deformed by being pressed by the outward flange 23c.

Besides, only one of the elastic members 32bb and 32dd in the annular shape may have the inclined surface with thickness of the elastic member decreasing toward a center of the annular shape.

Modified Example 2

In the above-described embodiment, the two elastic members 32b and 32d are provided between the two outward flanges 23c and 23d, and the elastic members 32b and 32d are deformed by being pressed by the outward flanges 23c and 23d, respectively, so that the diameters thereof are increased to close the gap g between the elastic members 32b, 32d and the inner wall of the cylinder 14. However, it may be configured such that, using one balloon which is an elastic body and has two valves, the gap g between the balloon and the inner wall of the cylinder 14 is closed.

Figure 15:
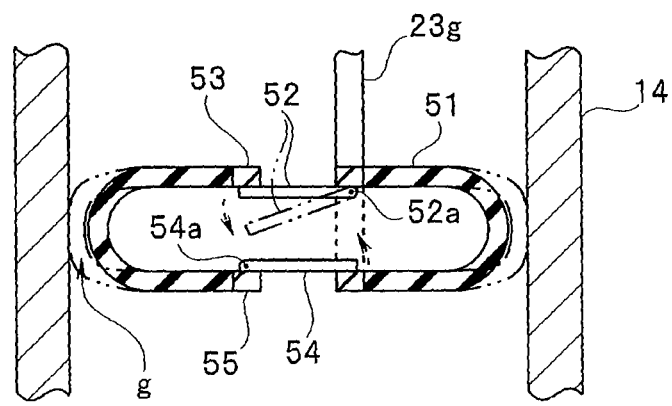
FIG. 15 is a cross sectional view of the distal end portion of the shaft portion 23 having a balloon which is an elastic body according to modified example 2 of the first embodiment of the present invention.

FIG. 15 is a cross sectional view of the distal end portion of the shaft portion 23 having the balloon which is the elastic body according to the modified example 2.

As shown in FIG. 15, a balloon 51 includes an annular member 53 which is fixed to a distal end part 23g provided at a distal end side of the shaft portion 23, and an annular member 55 which is provided to be distal with respect to the annular member 53 and fixed to the distal end part 23g of the shaft portion 23. A valve 52 is provided at the annular member 53 and a valve 54 is provided at the annular member 55.

The valves 52 and 54 are disposed inside of the balloon 51 which is a balloon member, and are attached to the annular members 53 and 55 to be pivotally supported by shaft 52a and 54a, respectively, such that the valves 52 and 54 open toward the inside when an external pressure becomes higher than an internal pressure of the balloon 51. In FIG. 15, the two-dot chain line shows a state in which the valve 52 of the annular member 53 is opened.

When the internal pressure and the external pressure of the balloon 51 are equal to each other, an outer diameter of the balloon 51 in a direction orthogonal to an axis of the cylinder 14 is smaller than the inner diameter of the distal end side part of the cylinder 14, and the gap g exists between an outer circumferential surface of the balloon 51 and the inner wall of the cylinder 14.

However, if there is clogging in the air feeding conduit 11, a liquid pressure on a proximal end side (i.e. on the air feeding conduit 11 side) of the balloon 51 increases. As a result, the valve 52 opens and the balloon 51 inflates to increase an outer diameter of the balloon 51 so that the gap g between the outer circumferential surface of the balloon 51 and the inner wall of the cylinder 14 is closed. In FIG. 15, it is shown by the two-dot chain line that the diameter of the balloon 51 increases and the gap between the outer circumferential surface of the balloon 51 and the inner wall of the cylinder 14 is closed.

In the same manner, if there is clogging in the water feeding conduit 12, a liquid pressure on a distal end side (i.e. on the water feeding conduit 12 side) of the balloon 51 increases. As a result, the valve 54 opens and the balloon 51 inflates to increase the outer diameter of the balloon 51 so that the gap g between the outer circumferential surface of the balloon 51 and the inner wall of the cylinder 14 is closed.

As described above, the partition portion is constituted by the balloon 51 as the close contact portion, the valve 52 provided at the air feeding conduit 11 side of the balloon 51, and the valve 54 provided at the water feeding conduit 12 of the balloon 51. The outer circumferential portion of the balloon 51 which is a balloon portion is spaced apart from the inner wall of the cylinder 14 by the predetermined distance when the internal pressure on the air feeding conduit 11 side and the internal pressure on the water feeding conduit 12 side correspond to each other. When the internal pressure on the air feeding conduit 11 side becomes higher than the internal pressure on the water feeding conduit 12 side, the valve 52 opens and the outer circumferential portion of the balloon 51 deforms by receiving the internal pressure on the air feeding conduit 11 side and comes in close contact with the inner wall of the cylinder 14, and when the internal pressure on the water feeding conduit 12 side becomes higher than the internal pressure on the air feeding conduit 11 side, the valve 54 opens and the outer circumferential portion of the balloon 51 deforms by receiving the internal pressure on the water feeding conduit 12 side and comes in close contact with the inner wall of the cylinder 14.

According to these modified examples, cleaning auxiliary tools capable of detecting clogging in each of the air feeding conduit and the water feeding conduit when performing the cleaning and disinfection, and securely cleaning and disinfecting the cylinder inner wall can be provided.

Modified Example 3

In the foregoing embodiments, the cleaning auxiliary tools that are applied to the cylinder 14 of the endoscope in which the first conduit 11 and the second conduit 12 communicate with each other are shown as examples, but the number of conduits of the endoscope is not limited to two and a cleaning auxiliary tool may be applied to a cylinder in which three or more conduits run in parallel and communicate with each other.

Figure 23:
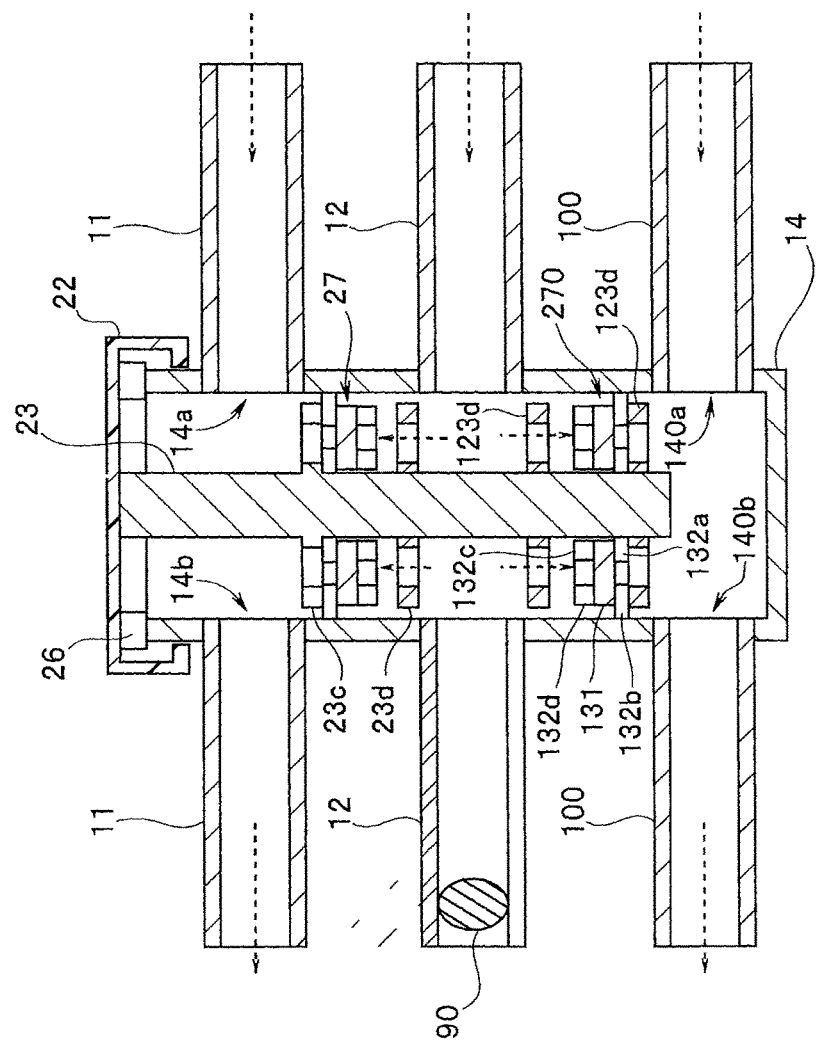
FIG. 23 is a schematic view for explaining an example of a cleaning auxiliary tool that is applied to a cylinder which is connected to a third conduit 100 in addition to a first conduit 11 and a second conduit 12.

FIG. 23 is a schematic view for explaining an example of a cleaning auxiliary tool that is applied to the cylinder 14 which is connected to a third conduit 100 as well as the first conduit 11 and the second conduit 12.

In the cylinder 14, a fifth opening 140a through which the liquid is introduced from the third conduit 100, and a sixth opening 140b through which the liquid is led out to the third conduit 100 are provided. Therefore, in the cleaning auxiliary tool according to the above-described embodiment, the shaft portion 23 further extends toward a bottom of the bottomed cylinder 14, a pair of outward flanges 123d are provided between the third opening 14c and the fifth opening 140a and between the fourth opening 14d and the sixth opening 140b, and a partition plate 270 arranged movable along the axial direction of the shaft portion 23 is provided between the pair of outward flanges 123d. The partition plate 270 is constituted by an annular member 131 and four elastic members 132a, 132b, 132c and 132d in an annular shape. The four elastic members 132a, 132b, 132c and 132d are fixed to the partition plate 270 in the same manner as the four elastic members 32a, 32b, 32c and 32d of the partition plate 27.

In FIG. 23, clogging 90 is caused in the second conduit 12, and therefore the partition plate 27 is moved to the first conduit 11 side and the partition plate 270 is moved to the third conduit 100 side, so that the liquid introduced into the cylinder 14 from the third opening of the second conduit 12 does not flow into the first conduit 11 and the third conduit 100. Thereby, the flow rate measured by the flow rate sensor 42 becomes 0 (zero) so that clogging can be detected.

Second Embodiment

In the first embodiment, if there is no clogging in the air feeding conduit 11 and the water feeding conduit 12, the partition plate 27 does not close the gap g between the partition plate 27 and the inner wall of the cylinder 14 so that the inner wall of the cylinder 14 is cleaned and disinfected by the cleaning solution or the like, and if there is clogging in the air feeding conduit 11 or the water feeding conduit 12, the partition plate 27 closes the gap g between the partition plate 27 and the inner wall of the cylinder 14 and the clogging is detected by the flow rate sensor.

By contrast, in the second embodiment, the partition plate is always in contact with the inner wall of the cylinder 14 without increasing the diameter thereof. Further, control is performed such that the liquid flows in the air feeding conduit 11 and the water feeding conduit 12 alternately, to change a position of an inner wall part with which the partition plate is in contact. As a result, the inner wall of the cylinder 14 is cleaned and disinfected such that there is not any part of the inner wall of the cylinder 14 that does not come in contact with the liquid, and it is configured such that, if there is clogging in the air feeding conduit 11 or the water feeding conduit 12, the clogging of the conduit can be detected by the flow rate sensor.

Since configurations of the endoscope and the cleaning auxiliary tool in the present embodiment are almost the same as the configuration of the endoscope and the cleaning auxiliary tool in the first embodiment, the same reference signs are assigned to the same elements and the description thereof is omitted, and a different configuration will be described.

Figure 16:
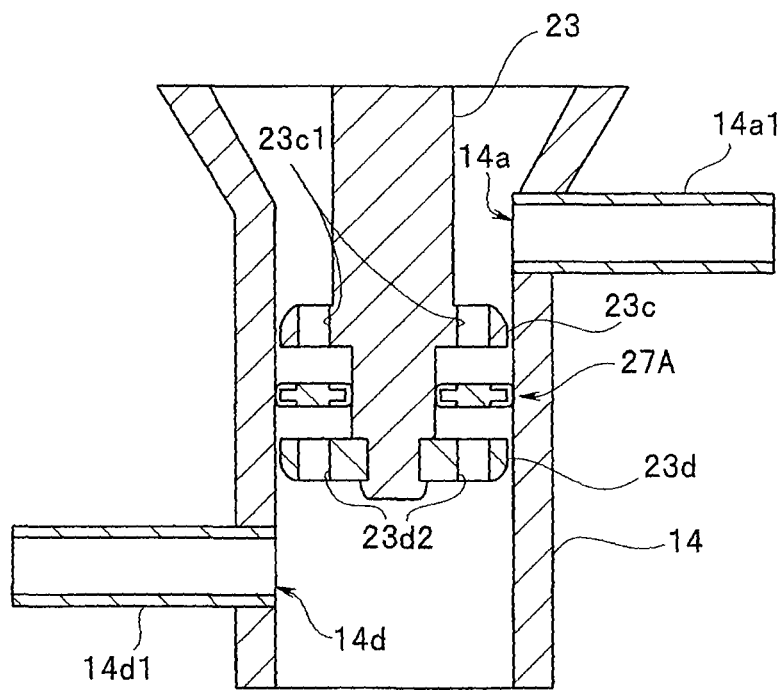
FIG. 16 is a cross sectional view of the distal end portion of the shaft portion 23 along the axial direction of the shaft portion 23 according to a second embodiment of the present invention.
Figure 17:
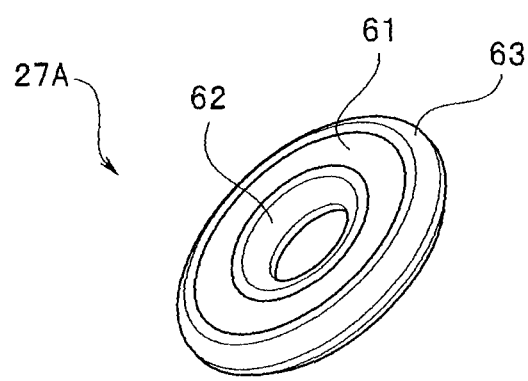
FIG. 17 is a perspective view of a partition plate 27A according to the second embodiment of the present invention.
Figure 18:
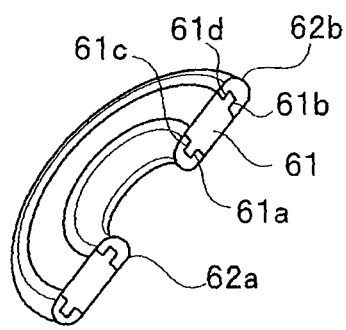
FIG. 18 is a cross-sectional perspective view of the partition plate 27A along the axial direction of the shaft portion 23 according to the second embodiment of the present invention.
Figure 19:
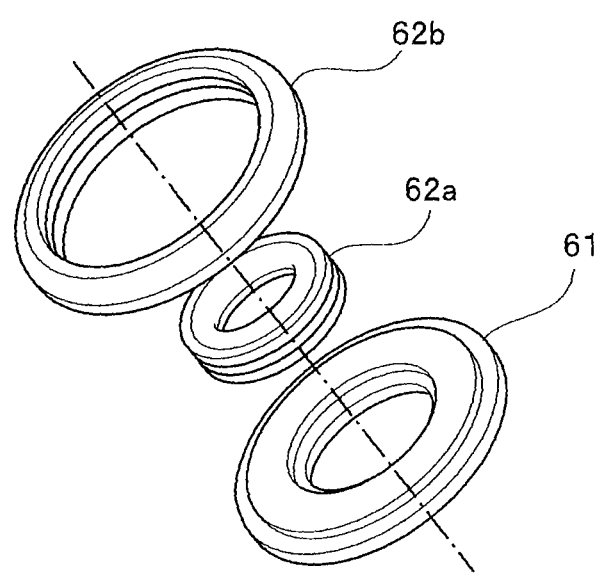
FIG. 19 is an exploded view of the partition plate 27 according to the second embodiment of the present invention.

FIG. 16 is a cross sectional view of the distal end portion of the shaft portion 23 along the axial direction of the shaft portion 23 according to the present embodiment. FIG. 17 is a perspective view of a partition plate 27A. FIG. 18 is a cross-sectional perspective view of the partition plate 27A along the axial direction of the shaft portion 23. FIG. 19 is an exploded view of the partition plate 27.

As shown in FIG. 19, the partition plate 27A of the separator unit 21 is configured to include an annular member 61, two annular seal members 62a and 62b (hereinafter, referred to as seal members 62 when referring to the two seal members as a whole or as seal member 62 when referring to arbitrary one of the seal members). The annular member 61 is made of resin and the seal member 62 is made of rubber.

Notch portions 61a and 61b are formed at an inner peripheral portion and an outer peripheral portion, respectively, on a distal-end-side surface of the annular member 61. Notch portions 61c and 61d are formed at an inner peripheral portion and an outer peripheral portion, respectively, on a proximal-end-side surface of the annular member 61.

An annular seal member 62a is adhered and fixed to the inner notch portions 61a and 61c of the annular member 61 by adhesive in such a manner as to cover the notch portions 61a and 61d from the inside. An annular seal member 62b is adhered and fixed to the outer notch portions 61b and 61d of the annular member 61 by adhesive in such a manner as to cover the notch portions 61b and 61d from the outside. An outer diameter of the seal member 62b is slightly larger than the inner diameter of the cylinder 14 and an outer circumferential surface of the seal member 62b is in contact with the inner diameter of the cylinder 14. That is, the partition plate 27A includes the annular member 61 which is a plate member and the seal member 62b provided at an outer circumferential portion of the annular member 61.

An inner diameter of the seal member 62a is smaller than an outer diameter of the extending portion 23e, and the annular partition plate 27A is a movable member that is provided between the outward flanges 23c and 23d movably along the axial direction of the shaft portion 23 by with the shaft portion 23 being inserted into a hole at a central portion of the partition plate 27A.

Figure 20:
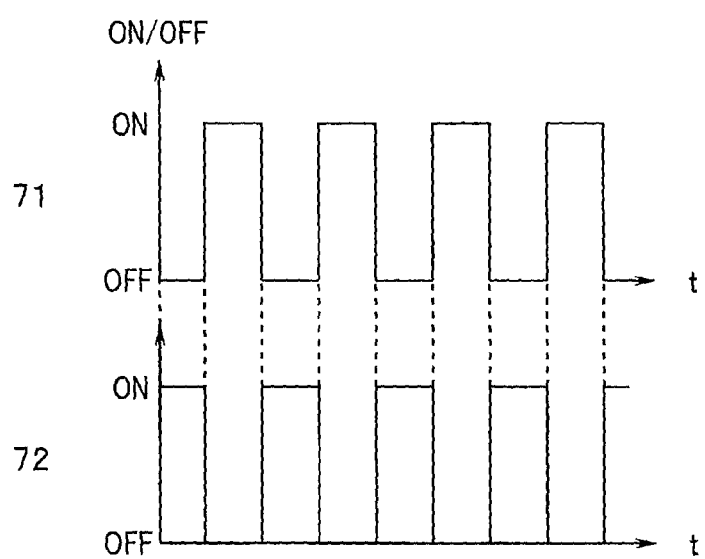
FIG. 20 is a time chart showing a control state of two liquid feeding pumps which feed the liquid such as a cleaning solution to the air feeding conduit 11 and the water feeding conduit 12 according to the second embodiment of the present invention.

Liquid feeding control of the air feeding conduit 11 and the water feeding conduit 12 will be described. FIG. 20 is a time chart showing a control state of two liquid feeding pumps which feed the liquid such as the cleaning solution to the air feeding conduit 11 and the water feeding conduit 12.

As shown in FIG. 20, a pump 71 for feeding the liquid to the air feeding conduit 11 is driven in such a manner as to switch between on and off alternately. On the other hand, a pump 72 for feeding the liquid to the water feeding conduit 12 is also driven in such a manner as to switch between on and off alternately so that timing of on and off of the pump 72 is inverse to timing of on and off of the pump 71.

Figure 21:
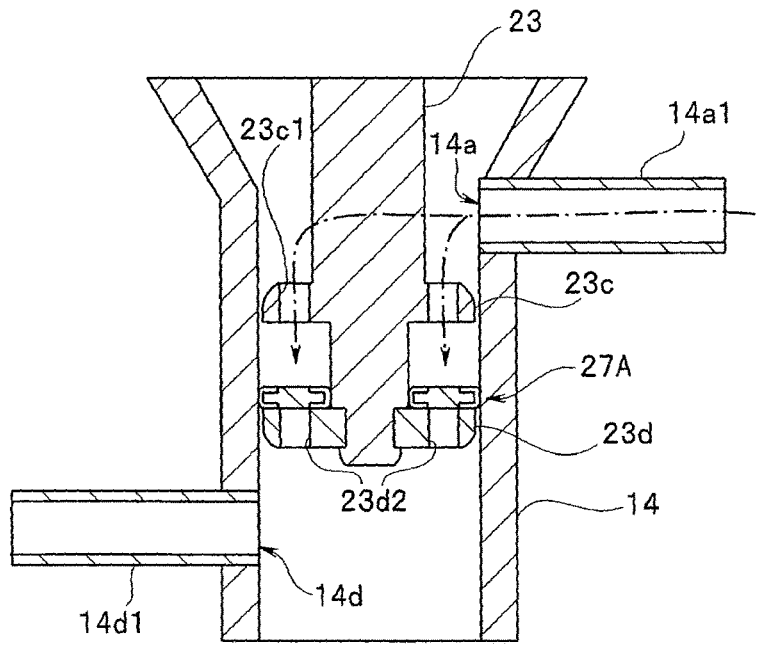
FIG. 21 is a cross sectional view of the distal end portion of the shaft portion 23 along the axial direction of the shaft portion 23 when a pump 71 is on and a pump 72 is off, according to the second embodiment of the present invention.
Figure 22:
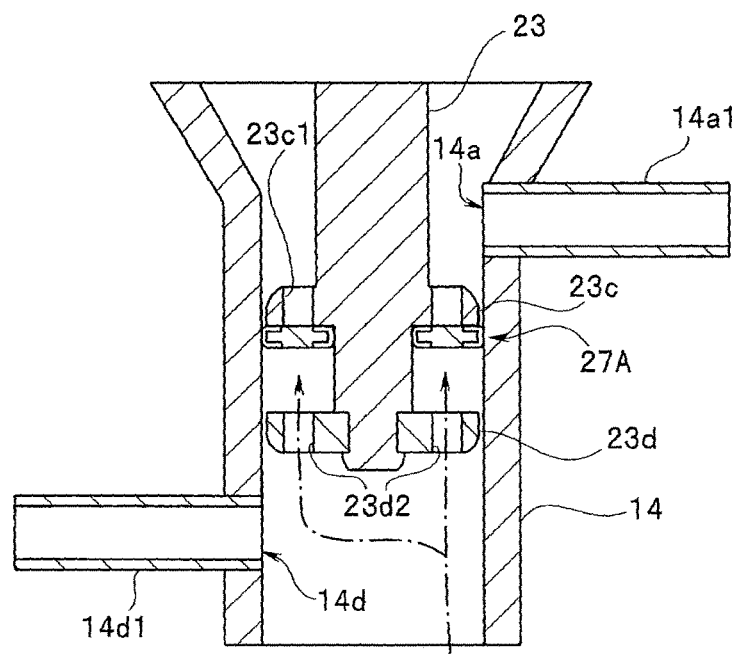
FIG. 22 is a cross sectional view of the distal end portion of the shaft portion 23 along the axial direction of the shaft portion 23 when the pump 71 is off and the pump 72 is on, according to the second embodiment of the present invention.

FIG. 21 is a cross sectional view of the distal end portion of the shaft portion 23 when the pump 71 is on and the pump 72 is off. FIG. 22 is a cross sectional view of the distal end portion of the shaft portion 23 when the pump 71 is off and the pump 72 is on.

As shown in FIG. 21, when the pump 71 is on and the pump 72 is off, a liquid pressure on a proximal end side of the partition plate 27A rises and a liquid pressure on a distal end side of the partition plate 27A does not rise, so that the partition plate 27A moves toward the outward flange 23d by the liquid flowing through the plurality of holes 23c1 of the outward flange 23c.

Further, as shown in FIG. 22, when the pump 71 is off and the pump 72 is on, the liquid pressure on the distal end side of the partition plate 27A rises and the liquid pressure on the proximal end side of the partition plate 27A does not rise, so that the partition plate 27A moves toward the outward flange 23c by the liquid flowing through the plurality of holes 23d2 of the outward flange 23d.

As shown in FIG. 20, the pumps 71 and 72 are not turned on at the same time, but are repeatedly turned on and off alternately, and therefore the partition plate 27A repeats advancing and retreating along the axial direction of the extending portion 23e of the shaft portion 23 in accordance with the on and off driving control of the pumps 71 and 72.

As a result, a position of contact between the seal member 62b on the outer circumferential side of the partition plate 27A and the inner wall of the cylinder 14 moves, and therefor there is not any part, on the inner wall of the cylinder 14, which does not come in contact with the liquid such as the cleaning solution. Thus, the liquid comes in contact with the entirety of the inner wall of the cylinder 14 and the inside of the cylinder 14 is completely cleaned and disinfected.

Thus, the partition plate 27A constitutes a partition portion that is provided at the distal end side of the shaft portion 23, is positioned between the first opening 14a and the third opening 14c and between the second opening 14b and the fourth opening 14d, partitions the air conduit 11 side and the water conduit 12 side in a state of being in close contact with the inner wall of the cylinder 14, moves toward the distal end side of the shaft portion 23 (i.e. the water feeding conduit 12 side) by receiving the internal pressure on the air feeding conduit 11 side when the internal pressure on the air feeding conduit 11 side becomes higher than the internal pressure on the water feeding conduit 12 side, and moves toward the proximal end side of the shaft portion 23 (i.e. the air feeding conduit 11 side) by receiving the internal pressure on the water feeding conduit 12 side when the internal pressure on the water feeding conduit 12 side becomes higher than the internal pressure on the air feeding conduit 11 side.

Further, if there is clogging in the air feeding conduit 11, the flow rate detected by the flow rate sensor 41 when the pump 71 is on becomes 0 (zero), and therefore the cleaning and disinfecting apparatus can detect the clogging of the air feeding conduit 11. In the same manner, if there is clogging in the water feeding conduit 12, the flow rate detected by the flow rate sensor 42 when the pump 72 is on becomes 0 (zero), and therefore the cleaning and disinfecting apparatus can detect the clogging of the water feeding conduit 12.

Hence, also in the present embodiment, it is possible to provide the cleaning auxiliary tool that is capable of detecting clogging in each of the air feeding conduit and the water feeding conduit when performing the cleaning and disinfecting, and capable of securely cleaning and disinfecting the inner wall of the cylinder.

Third Embodiment

In the first embodiment and the second embodiment, the cleaning auxiliary tools each applied to the endoscope cylinder in which the first conduit 11 and the second conduit 12 run in parallel, and the four openings of the first opening 14a, the second opening 14b, the third opening 14c and the fourth opening 14d are formed are described.

By contrast, the third embodiment concerns a cleaning auxiliary tool that is applied to an endoscope cylinder 14 in which the second conduit 12 runs in parallel from an intermediate position of the first conduit 11, and the third opening 14c, which is present in the first embodiment, is not formed.

Figure 24:
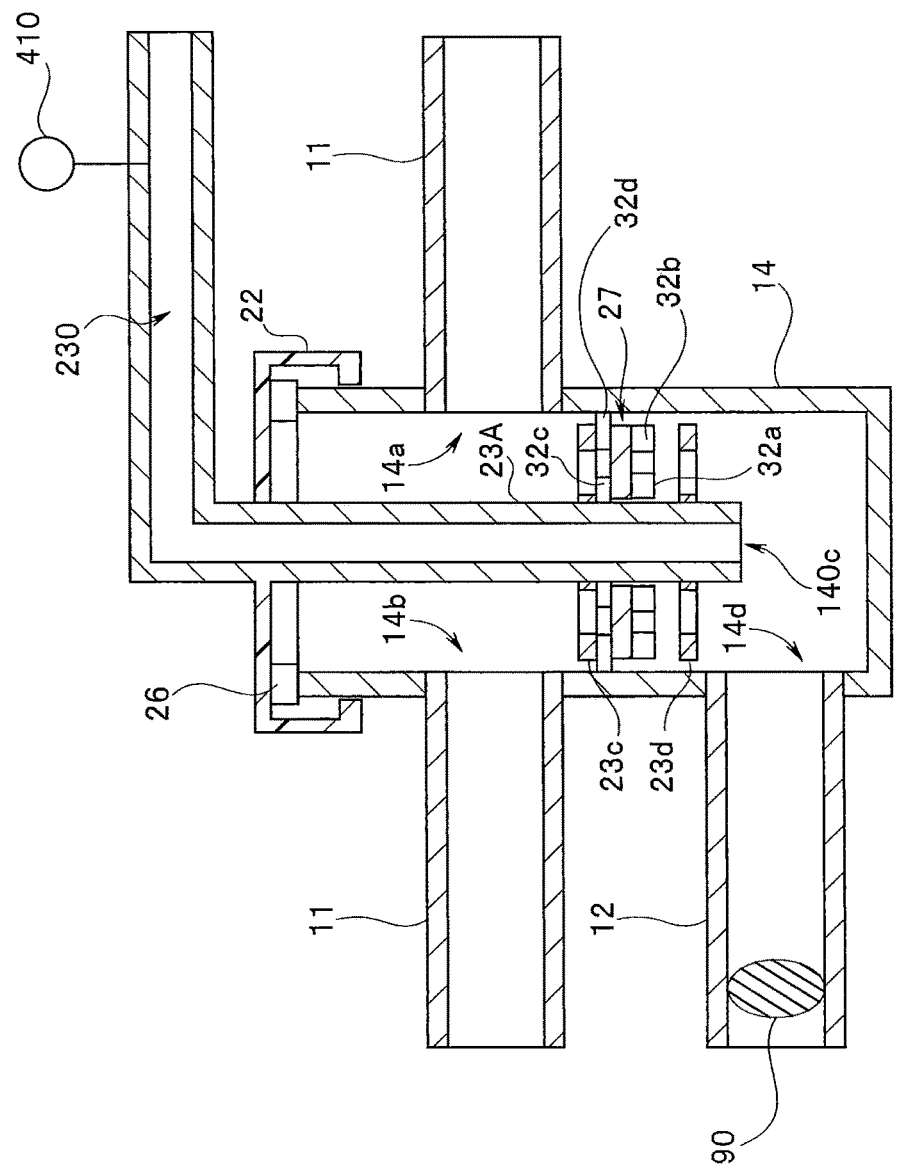
FIG. 24 is a schematic view for explaining configuration of a cleaning auxiliary tool that is applied to an endoscope cylinder in which the second conduit 12 runs in parallel from an intermediate position of the first conduit 11 and a third opening 14c, which is present in the first embodiment, is not formed.

FIG. 24 is a schematic view for explaining the configuration of the cleaning auxiliary tool that is applied to the endoscope cylinder in which the second conduit 12 runs in parallel from the intermediate position of the first conduit 11 and the third opening 14c, which is present in the first embodiment, is not formed. As shown in FIG. 24, the cylinder 14 to which the cleaning auxiliary tool of the present embodiment is applied has the first opening 14a and the second opening 14b which communicate with the first conduit 11, and the fourth opening 14d which communicates with the second conduit 12. In a state where the button such as the air/water feeding button 6 or the suction button 7 is attached to the cylinder 14 in the present embodiment, the liquid introduced into the cylinder from the first conduit 11 is introduced into the second opening 14b or the fourth opening 14d by switching using the button.

The pair of the outward flange 23c and the outward flange 23d, the partition plate 27 provided at the shaft portion 23A, and the elastic members 32b and 32d are the same as those in the first embodiment, and performs the same operations as in the first embodiment.

However, in order to flow the liquid evenly through the first conduit 11 and the second conduit 12, in the third embodiment, a shaft portion 23A has a tubular shape to form an in-shaft conduit 230, and it is possible to lead out the liquid from an opening 140c at a distal end of the shaft portion 23A by connecting the shaft portion 23A to a liquid supply source. Thus, it is possible to flow the liquid through the second conduit 12 from the shaft portion 23A by attaching the cleaning auxiliary tool to the cylinder 14.

A flow rate sensor for detecting a flow rate of the liquid flowing through the in-shaft conduit 230 of the shaft portion 23A may be arranged at the shaft portion 23A or the liquid supply source connected to the shaft portion 23A. As shown in FIG. 24, if clogging 90 is caused in the second conduit 12, the clogging in the second conduit 12 can be detected by a flow rate sensor 410 arranged at the shaft portion 23A or the liquid supply source. A fluid supply source herein referred to includes the endoscope cleaning and disinfecting apparatus, for example.

As shown in FIG. 4, the flow rate sensor 41 is connected to the upstream side of the air feeding conduit 11 so as to measure the flow rate of the liquid flowing through the air feeding conduit 11. The flow rate sensor 42 is connected to the upstream side of the water feeding conduit 11 so as to measure the flow rate of the liquid flowing through the water feeding conduit 12

Hence, according to the present embodiment also, it is possible to provide the cleaning auxiliary tool that is capable of detecting clogging in each of the air feeding conduit and the water feeding conduit when performing the cleaning and disinfecting, and capable of securely cleaning and disinfecting the cylinder inner wall.

The present invention is not limited to the above-described embodiments, and may be subjected to various changes and modifications in a range where the gist of the invention is not changed.

What is claimed is:

1. A cleaning auxiliary tool to be inserted into a bottomed cylinder having a bottomed cylindrical shape with one end opened and other end closed, the bottomed cylinder having a first opening through which a fluid from a first conduit is introduced, the first conduit being inserted through an endoscope, a second opening through which the fluid is led out into the first conduit, a third opening through which the fluid from a second conduit is introduced, the second conduit running in parallel with the first conduit in the endoscope, and a fourth opening through which the fluid is led out into the second conduit, the cleaning auxiliary tool comprising:
  a lid portion that closes an opening of the bottomed cylinder;
  a shaft portion having a first end portion connected to the lid portion and a second end portion extending into the bottomed cylinder;
  a first plate member fixed to the shaft portion, the first plate member having a first outer diameter smaller than an inner diameter of the bottomed cylinder;
  a second plate member fixed to the shaft portion and arranged closer to the first conduit than the first plate member, the second plate member having a second outer diameter smaller than the inner diameter of the bottomed cylinder; and
  a partition portion provided between the first plate member and the second plate member and positioned between the first opening and the third opening and between the second opening and the fourth opening, that partitions a side of the first conduit and a side of the second conduit in a state of being in close contact with an inner wall of the bottomed cylinder, moves toward the second end portion of the shaft portion by receiving an internal pressure on the side of the first conduit when the internal pressure on the side of the first conduit becomes higher than an internal pressure on the side of the second conduit, and moves toward the first end portion of the shaft portion by receiving the internal pressure on the side of the second conduit when the internal pressure on the side of the second conduit becomes higher than the internal pressure on the side of the first conduit, the partition portion,
  when moving toward the second end portion and when moving toward the first end portion, contacts the inner wall with an outer circumferential portion of the partition portion, and axially moves along the shaft portion a distance sufficient to allow the fluid to contact the entire inner wall disposed between the first plate member and the second plate member.

2. The cleaning auxiliary tool according to claim 1, wherein the partition member includes a third plate member and a seal member provided at an outer circumferential portion of the third plate member.

3. The cleaning auxiliary tool according to claim 1, further comprising a fixing member for fixing the cleaning auxiliary tool to the bottomed cylinder.

* * * * *